United States Patent [19]

Siegrist et al.

[11] Patent Number: 5,484,918
[45] Date of Patent: Jan. 16, 1996

[54] PROCESS FOR THE PREPARATION OF AQUEOUS NICOTINALDEHYDE

[75] Inventors: Urs Siegrist, Eiken; Henry Szczepanski, Wallbach, both of Switzerland

[73] Assignee: Ciba-Geigy Corporation, Ardsley, N.Y.

[21] Appl. No.: 194,191

[22] Filed: Feb. 9, 1994

[30] Foreign Application Priority Data

Mar. 2, 1993 [GB] United Kingdom ............. 9304191

[51] Int. Cl.$^6$ ............................................. C07D 253/06
[52] U.S. Cl. ..................................... 544/182; 544/183
[58] Field of Search ............................ 544/182, 183

[56] References Cited

U.S. PATENT DOCUMENTS

| | | | |
|---|---|---|---|
| 2,798,077 | 7/1957 | Schläpfer et al. | 260/296 |
| 2,945,862 | 7/1960 | Mignonac et al. | 260/297 |
| 3,274,206 | 9/1966 | Wilbert et al. | 260/297 |

FOREIGN PATENT DOCUMENTS

| | | |
|---|---|---|
| 0087298 | 8/1983 | European Pat. Off. . |
| 0314615 | 5/1989 | European Pat. Off. . |
| 0043044 | 1/1966 | Germany . |
| 9202507 | 2/1992 | WIPO . |

OTHER PUBLICATIONS

Reaktionen der Organischen Synthese, 92 (1978).
Chem. Ber. 102:2770–2776 (1969), Tinapp.
Plieninger et al., Berichte der Deutschen Chemischen Gesellschaft, vol. 88, p. 1956 (1955).
Mathes et al., Chemiker–Zeitung, vol. 80, p. 475 (1956).
Derwent Abst. 92–092944/12 (Corresponding to JP–4,036, 250) May 30, 1990.
Chem. Abst. 80:120705g, Volkova et al., p. 416, (1974).

*Primary Examiner*—John M. Ford
*Attorney, Agent, or Firm*—Marla J. Mathias

[57] ABSTRACT

A process for the preparation of an aqueous medium of nicotinaldehyde by the catalytic reduction of 3-cyanopyridine under hydrogen in the presence of Raney-nickel.

6 Claims, No Drawings

PROCESS FOR THE PREPARATION OF AQUEOUS NICOTINALDEHYDE

The present invention relates to a process for the preparation of an aqueous medium of nicotinaldehyde of the formula I

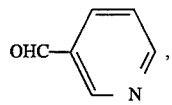

by the catalytic hydrogenation of 3-cyanopyridine of the formula II

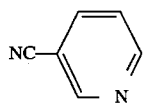

in the presence of Raney-nickel in an aqueous medium of a carboxylic acid.

Nicodnaldehyde (3-pyridinaldehyde) is a useful reagent in the synthesis of agrochemicals. For example the insecticide 6-methyl-4-(pyridin-3-yl-methyleneamino)-4,5-dihydro1,2,4 -triazin-3(2H)-one can be prepared by the reaction between nicotinaldehyde and the aminotriazinone 4-amino-6-methyl-3-oxo-2,3,4,5-tetrahydro-1,2,4-triazine as described in published European patent application EP-A-0 3 14 615.

A synthesis of nicotinaldehyde by hydrogenation of the corresponding nitrile, namely 3-cyanopyridine, is described in U.S. Pat. No. 2,945,862 in which strongly acidic conditions are advocated. Sulfuric or oxalic acids are described as providing suitable conditions and the yields are not of a high order. C. Ferri describes in Reakfionen der organisthen Synthese, p. 92, (1978) the catalytic hydrogenation of aromatic nitriles, including cyanopyridines, to the corresponding aldehydes in the presence of Raney-nickel. Again strongly acidic conditions are proposed using sulfuric, oxalic or sulfonic acids. The strong acids poison the Raney-nickel catalyst which suppresses the formation of side products. P. Tinapp describes in Chem. Ber., 102, p. 2770 to 2776 (1969) the hydrogenation of aromatic nitriles with Raney-nickel in the presence of different acids. The selective saturation of the carbon-nitrogen triple bond occurs only in the presence of strong acids, and no partial hydrogenation was observed in the presence of acetic acid.

A process is described in published PCT application WO 92/02507 in which aldehydes are prepared by hydrogenating a mixture of a 3-cyanopyridine and a primary amine in the presence of a rhodium-loaded catalyst to form a stable imine intermediate. The hydrogenation catalyst is separated from the irainc intermediate and this intermediate is then hydrolysed to the corresponding aldehyde. However the yields are low and the use of rhodium in industrial production processes is extremely expensive.

There is a need for an improved nicotinaldehyde synthesis which is more economical and ecologically acceptable. The disadvantages of the known processes include low selectivity, poor yields and corrosion of the nickel catalyst and the production vessels.

Surprisingly it has now been found that a high concentration of nicotinaldehyde can be achieved under milder reaction conditions with superior yields and a higher degree of selectivity. It has also been found that use of expensive rhodium-loaded catalysts is not necessary.

The object of the present invention is to provide a process for the preparation of an aqueous medium of 10 to 60% nicotinaldehyde by weight by the catalytic reduction of 3-cyanopyridine under hydrogen in the presence of Raney-nickel, characterized in that a) the Raney-nickel catalyst is present in an amount between 2 and 10 weight-% with respect to the cyanopyridine, b) the solvent is aqueous carboxylic acid, c) the pH is between 3.5 and 7, d) the temperature is less than or equal to 40 ° C, e) the hydrogen pressure is between 0.2 and 5 bar, f) the amount of hydrogen taken up is up to 110% with respect to the cyanopyridine, and g) the amount of water present is in excess with respect to the cyanopyfidine.

The process can be conducted continuously or batchwise. A batchwise process is preferred. The product of the process according to the invention can be used directly for further synthesis steps, or stored prior to further use.

The amount of nicotinaldehyde in the aqueous medium is preferably 20 to 50 wt-%, more preferably 25 to 40 wt-%.

The Raney-nickel is present in an amount preferably between 3 and 7 wt-% with respect to the cyanopyridine. The Raney-nickel is stored under water prior to use.

The carboxylic acid can be present in stoichiometric or slightly sub-stoichiometric amounts or in excess with respect to the cyanopyridine. Stoichiometric amounts are preferred. Carboxylic acids form a buffer with ammonia. The pH rises quickly to about 5 during the course of the inventive process, and it is surprising that the reaction runs to completion at this pH without further addition of carboxylic acid. The pH may also be controlled by continuous addition of a carboxylic acid. Examples of aqueous carboxylic acid mixtures may contain an unlimited amount of $C_1$–$C_6$alcohols and a $C_1$–$C_6$carboxylic acid. The solvent is preferably aqueous acetic acid.

The temperature is preferably between 10 and 30 ° C, and more preferably between 20 and 30 ° C. The hydrogen pressure is preferably between 0.5 and 3 bar, more preferably between 0.5 and 1.5 bar. The water content with respect to the cyanopyridine is preferably up to 60% excess by weight, more preferably up to 40 wt-%. The reaction time is typically between 3 and 6 hours.

The carboxylic acids are non-corrosive to the nickel catalyst in contrast to prior art processes in which a corrosive medium is present, e.g. mineral acids. A particular disadvantage of hydrochloric acid in this area is the production of ammonium chloride which causes further corrosion of the production vessel.

The advantages of this process are as follows:

i) nicotinaldehyde is formed as a storage-stable solution, ii) no corrosive ammonium chloride is produced, iii) a very low concentration of nickel catalyst is required, iv) high reaction selectivity, resulting in a decrease in the quantity of side-products produced, v) high aldehyde yield, vi) low contamination of the aldehyde solution with nickel, and vii) a high volume throughput increases production capacity thereby reducing unit costs.

It is a further object of the present invention to provide a process for the preparation of a compound of formula III

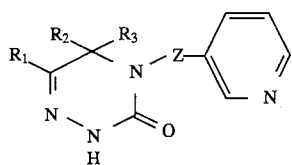

wherein $R_1$ is hydrogen, $C_1$–$C_{12}$alkyl, $C_3$–$C_6$cycloalkyl, $C_1$–$C_4$ alkoxy-$C_1$–$C_6$alkyl, $C_1$–$C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$–$C_5$alkyl, $C_1$–$C_2$haloalkyl, methoxy and/or ethoxy, $R_2$ is hydrogen, $C_1$–$C_6$alkyl or $C_3$–$C_6$cycloalkyl, or is phenyl that is unsubstituted or substituted by $C_1$–$C_{12}$alkyl, halogen or by $C_1$–$C_{12}$haloalkyl, or $R_1$ and $R_2$ together form a saturated or unsaturated 3- to 7-membered carbocycle, $R_3$ is hydrogen or $C_1$–$C_6$alkyl and Z is —N=CH— or —NH—CH$_2$—, which process comprises reacting an aminotriazinone of formula IV

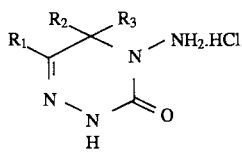

wherein $R_1$, $R_2$ and $R_3$ have the meanings above with an aldehyde of formula V

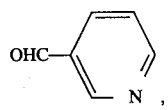

and, if desired, converting the resulting pyridyl-methyleneamino-triazinone by selective reduction into pyridyl-methylamino-triazinone, wherein the aldehyde of formula V is prepared by the catalytic reduction of 3-cyanopyridne under hydrogen in the presence of Raney-nickel, characterised in that
a) the Raney-nickel catalyst is present in an amount between 2 and 10 weight-% with respect to the cyanopyridine,
b) the solvent is aqueous carboxylic acid,
c) the pH is between 3.5 and 7,
d) the temperature is less than or equal to 40 °C.,
e) the hydrogen pressure is between 0.2 and 5 bar,
f) the mount of hydrogen taken up is up to 110% with respect to the cyanopyridine, and
g) the amount of water present is in excess with respect to the cyanopyridine.

Preferred compounds of the formula III are those wherein $R_1$ is hydrogen, $C_1$–$C_6$alkyl, $C_3$–$C_5$cycloalkyl, phenyl or phenyl that is mono-or di-substituted by halogen, $C_{1–C3}$alkyl, methoxy or ethoxy, each of $R_2$ and $R_3$ is hydrogen or $C_{1–C4}$alkyl and Z is —N=CH— or —NH—CH$_2$—, more preferred are those compounds of the formula III wherein $R_1$ is hydrogen, $C_1$–$C_4$alkyl, cyclopropyl or phenyl; $R_2$ is hydrogen, methyl or ethyl; and $R_3$ is hydrogen or methyl; and Z is —N=CH—or —NH—CH$_2$—; most preferred is 6-methyl-4-(pyridin-3-yl- methyleneamino)-4,5-dihydro- 1,2,4-triazin-3(2H)-one.

A preferred embodiment of the present invention is a process wherein the aminotriazinone of the formula IV is prepared by the solvolysis of a compound of formula VI

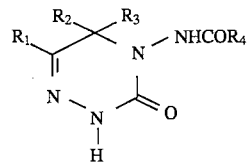

wherein $R_1$, $R_2$ and $R_3$ have the meanings given above and $R_4$ is H, $C_{1–C4}$-alkyl, $C_3$–$C_6$-cycloalkyl, $C_1$–$C_4$-alkyl substituted by 1 to 9 chlorine atoms, $C_1$–$C_3$-alkoxy, $C_1$–$C_3$-alkylthio, phenyl, pyridyl, or phenyl or pyridyl which is substituted with 1 to 3 substituents selected from the group of halogen, methyl, ethyl, methoxy, methylthio or nitro, in the presence of hydrogen chloride, which is preferably gaseous, in an alcoholic medium.

The alcoholic medium can consist of one or more primary, secondary or tertiary alcohols. Examples are methanol, ethanol, n-propanol, isopropanol, n-butanol, n-pentanol or a mixture of these. Methanol is preferred.

If gaseous hydrogen chloride is used the reaction medium of the solvolysis can be anhydrous or contain very small amounts of water so that the water content can be between 0 and 5 weight-% with respect to the acetyltriazinone of formula VI. Substantially dry conditions, i.e. 0 to 3 wt-% water content are preferred, more preferably 0 to 2 wt-% with respect to the acetyltriazinone of formula VI. Anhydrous conditions, i.e. 0 wt-% water content, are particularly preferred.

The solvolysis reaction can be conducted at a temperature between 0 ° C and the boiling point of the solvent used. The preferred temperature range is 40 to 50 ° C.

If gaseous hydrogen chloride is used dry HCl gas is bubbled into the reaction mixture and uureacted HCl is recycled. The reaction conditions remain non-corrosive to the reaction vessel on account of the zero or very low water content.

The process according to the invention can be conducted in a batchwise or continuous manner. Batchwise production is preferred.

An almost quantitative conversion is obtained by the formation and precipitation of the aminotriazinone as its hydrogen chloride salt, combined with the formation of the ester of the displaced-COR$_2$ group.

The following Examples demonstrate the process of the invention.

The aldehyde yield is determined by HPLC or gravimetrically by derivatisation with 4-amino-6-methyl-3-oxo-2,3,4, 5-tetrahydro-1,2,4-triazine, abbreviated aminotriazinone.

EXAMPLE 1

(lab scale)

124.8 g 3-cyanopyridine, 277 g water and 72.2 g acetic acid are mixed together in a stirring autoclave. 14.6 g moist Raney-nickel (Ni contents about 60%) in 50 g water are added to the mixture which is then hydrogenated under a constant hydrogen pressure of 1 bar. When 110% of the theoretical hydrogen quantity have been taken up (after about 5 hours), the stirrer is switched off and the reaction mixture quenched with nitrogen. The catalyst is filtered off under an argon atmosphere and rinsed with water. 515 g product solution are obtained after filtration with 20.9%

3-pyridinaldehyde as determined by HPLC. This represents a yield of 85.2% of theory. The proportion of 3-picolylalcohol is 0.4% and that of 3-picolylamine 1.5%. The aldehyde yield is found to be 84% after derivatisation with aminotriazinone. The nickel loss of the catalyst is 115 mg, corresponding to ca. 1.3% of the total nickel content.

EXAMPLE 2

(pilot plant scale)

The procedure used in Example 1 is repeated except that 200 kg 3-cyanopyridine are used and corresponding amounts of the other reagents are added (a 1600-fold scale-up). After filtration 873 kg product solution are obtained with a 22.0% content of 3-pyridinaldehyde (yield 93.3% of theory). The 3-picolylamine content in the solution is 1.1% and that of 3-picolylalcohol 0.1%. The nickel loss from the catalyst is 0.5% of the total nickel content.

EXAMPLE 3

(at constant pH 5)

104 g 3-cyanopyridine and 200 g water are combined in a stirring autoclave. 12.1 g moist Raney-nickel (Ni contents about 60%) in 42 g water are added to the reaction mixture which is hydrogenated at room temperature under a constant hydrogen pressure of 1 bar. 191 g acetic acid are added in order to maintain a constant pH 5. When 110% of the theoretical hydrogen quantity has been taken up, the stirrer is switched off and the reaction mixture quenched with nitrogen. The catalyst is filtered off under an argon atmosphere and rinsed with water. After filtration there are obtained 561 g 3-pyridinaldehyde solution. The aldehyde yield is found to be 80% after derivatisation of 140.2 g of the solution with aminotriazinone. The nickel lost from the catalyst is 42 mg, corresponding to ca. 0.6% of the total nickel content.

EXAMPLE 4

(at 5 bar hydrogen pressure)

The procedure of Example 1 is followed except that the hydrogen pressure is maintained at a constant 5 bar. After filtration, a product solution is obtained with 14% 3-pyridinaldehyde as determined by HPLC, representing a yield of 64%. The aldehyde yield is 68% after derivatisation with aminotriazinone.

EXAMPLE 5

(at pH 4.7 to 7)

The procedure of Example 1 is followed except that 57.6 g acetic acid and 19.6 g sodium acetate are added. The aldehyde yield after derivatisation with aminotriazinone is 73%. The nickel lost from the catalyst is ca. 0.5% by weight of the total nickel content.

EXAMPLE 6

(concentration of 50% 3-cyanopyridine in water)

The procedure of Example 1 is followed except that 31.2 g 3-cyanopyridine and 31.2 g water are used. After derivatisation with aminotriazinone, the aldehyde yield is found to be 82%.

EXAMPLE 7

(catalyst recycled)

The procedure of Example 1 is repeated. When 110% of the theoretical amount of hydrogen have been taken up, the reaction is quenched with nitrogen and the hydrogenation solution filtered through a 0.5 gm sintered metal plate (surface area 4.5 cm$^2$) at the reactor base. By addition of 3-cyanopyridine, water and acetic acid, the same catalyst is used as in Example 1 repeatedly. The aldehyde yield from the fast three repeat cycles, in which the hydrogenation time is almost constant, is found to be 76% by derivatisation with aminotriazinone.

Example 8

Preparation of 4-amino-6-methyl-3-oxo-2,3,4,5-tetrahydro-1,2,4-triazine

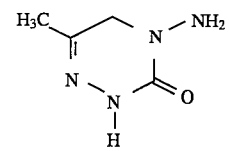

A suspension is prepared of 39.9 g (0.234 mol) 6-methyl-4-acetylamino-4,5-dihydro1,2,4 -triazin-3-(2H)-one in 99 g 95 % methanol the suspension is heated to 45° C. and becomes a clear colourless solution. At between 45 and 50 ° C. a total of 15.4 g (0.421 mol) HCl are bubbled through this solution over a 2 to 3 hour period. After about 30% of the HCl has been added the reaction mixture is seeded with 4-amino-6-methyl-3-oxo-2,3,4,5-tetrahydro-1,2,4 -triazine hydrochloride. Thereafter 4-amino-6-methyl-3-oxo-2,3,4,5-tetrahydro-1,2,4 -triazine precipitates out continuously as the hydrochloride salt. After about 2 hours stirring, the maximum conversion of over 99% is reached. The reaction mixture is brought to pH 5 by the addition of 50% NaOH solution. The free aminotriazinone 4-amino-6-methyl-3-oxo-2,3,4,5-tetrahydro-1,2,4-triazine is formed in an amount of 29.7 g representing 14.3% by weight of the solution. This represents a yield of 99.2% of theory.

EXAMPLE 9

Preparation of 6-methyl-4-(pyridin-3-ylmethyleneamino)-4,5-dihydro1,2,4-triazin- 3 ( 2H)-one To a suspension of 164 g of 4-amino-6-methyl-3-oxo-2, 3,4,5-tetrahydro-1,2,4-triazine hydrochloride in 500 ml methanol a 50% NaOH solution is added until a pH of 6 is reached. Now 486 g of a solution containing 22% 3-pyridinaldehyde in water is added maintaining a temperature below 70° C. After the addition is completed the reaction mixture is kept at 65° C. for two hours. Then the suspension is cooled to about 5° C., filtered and dried to yield the title compound.

What is claimed is:

1. A process for the preparation of a compound of formula III

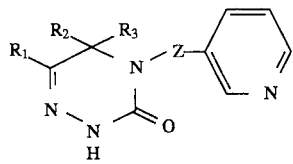

wherein $R_1$ is hydrogen, $C_1$–$C_{12}$alkyl, $C_3$–$C_6$ cycloalkyl, $C_1$–$C_4$alkoxy-$C_1$–$C_6$alkyl, $C_1$–$C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$–$C_5$alkyl, $C_1$–$C_2$haloalkyl, methoxy and/or ethoxy; $R_2$ is hydrogen, $C_1$–$C_6$alkyl or $C_3$–$C_6$cycloalkyl, or is phenyl that is unsubstituted or substituted by $C_1$–$C_{12}$alkyl, halogen or by $C_1$–$C_{12}$haloalkyl; or $R_1$ and $R_2$ together form a saturated or unsaturated 3- to 7-membered carbocycle; $R_3$ is hydrogen or $C_1$–$C_6$alkyl and Z is —N=CH— or —NH—$CH_2$—, which process comprises reacting an aminotriazinone of formula IV

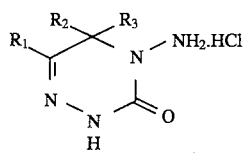

wherein $R_1$, $R_2$ and $R_3$ have the meanings above with an aldehyde of formula V

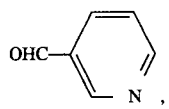

and, if desired, converting the resulting pyridyl-methyleneamino-triazinone by selective reduction into pyridyl-methylamino-triazinone, wherein the aldehyde of formula V is prepared by the catalytic reduction of 3-cyanopyridine under hydrogen in the presence of Raney-nickel, characterised in that
 a) the Raney-nickel catalyst is present in an mount between 2 and 10 weight-% with respect to the cyanopyridine,
 b) the solvent is aqueous carboxylic acid,
 c) the pH is between 3.5 and 7,
 d) the temperature is less than or equal to 40 °C.,
 e) the hydrogen pressure is between 0.2 and 5 bar,
 f) the amount of hydrogen taken up is up to 110% with respect to the cyanopyridine, and
 g) the amount of water present is in excess with respect to the cyanopyridine.

2. A process according to claim 1 wherein $R_1$ is hydrogen, $C_1$–$C_6$alkyl, $C_3$–$C_5$cycloalkyl, phenyl or phenyl that is mono- or di-substituted by halogen, $C_1$–$C_3$alkyl, methoxy or ethoxy, each of $R_2$ and $R_3$ is hydrogen or $C_1$–$C_4$alkyl and Z is —N=CH— or —NH—$CH_2$—.

3. A process according to claim 2 wherein $R_1$ is hydrogen, $C_1$–$C_4$alkyl, cyclopropyl or phenyl; $R_2$ is hydrogen, methyl or ethyl; and $R_3$ is hydrogen or methyl; and Z is —N=CH— or —NH—$CH_2$—.

4. A process according to claim 3 wherein the compound of formula III is 6-methyl-4-(pyridin-3-ylmethyleneamino)-4,5-dihydro-1,2,4-triazin-3(2H)-one.

5. A process according to claim 1 wherein the aminotriazinone of the formula IV is prepared by the solvolysis of a compound of formula VI

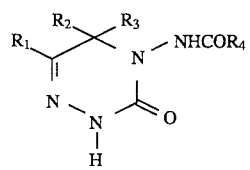

wherein $R_1$ is hydrogen, $C_1$–$C_{12}$alkyl, $C_3$–$C_6$cycloalkyl, $C_1$–$C_4$alkoxy-$C_1$–$C_6$alkyl, $C_1$–$C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$–$C_5$alkyl, $C_1$–$C_2$haloalkyl, methoxy and/or ethoxy; $R_2$ is hydrogen, $C_1$–$C_6$alkyl or $C_3$–$C_6$cycloalkyl, or is phenyl that is unsubstituted or substituted by $C_1$–$C_{12}$alkyl, halogen or by $C_1$–$C_{12}$haloalkyl; or $R_1$ and $R_2$ together form a saturated or unsaturated 3- to 7-membered carbocycle; $R_3$ is hydrogen or $C_1$–$C_6$alkyl; and $R_4$ is H, $C_1$–$C_4$-alkyl, $C_3$–$C_6$-cycloalkyl, $C_1$–$C_4$-alkyl substituted by 1 to 9 chlorine atoms, $C_1$–$C_3$-alkoxy, $C_1$–$C_3$-alkylthio, phenyl, pyridyl, or phenyl or pyridyl which is substituted with 1 to 3 substituents selected from the group of halogen, methyl, ethyl, methoxy, methylthio or nitro, in the presence of hydrogen chloride in an alcoholic medium.

6. A process according to claim 5 wherein the hydrogen chloride is gaseous.

\* \* \* \* \*